(12) United States Patent
Arora et al.

(10) Patent No.: US 9,931,333 B2
(45) Date of Patent: Apr. 3, 2018

(54) COMPOSITIONS AND METHODS FOR TREATING OR PREVENTING ATRIAL FIBRILLATION

(71) Applicant: Northwestern University, Evanson, IL (US)

(72) Inventors: Rishi Arora, Chicago, IL (US); David E. Zembower, La Grange, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/333,953

(22) Filed: Oct. 25, 2016

(65) Prior Publication Data
US 2017/0100387 A1    Apr. 13, 2017

Related U.S. Application Data

(63) Continuation of application No. 13/106,618, filed on May 12, 2011.

(60) Provisional application No. 61/334,023, filed on May 12, 2010, provisional application No. 61/409,691, filed on Nov. 3, 2010.

(51) Int. Cl.
| | |
|---|---|
| *A61K 31/46* | (2006.01) |
| *A61K 31/138* | (2006.01) |
| *A61K 31/137* | (2006.01) |
| *A61K 31/132* | (2006.01) |

(52) U.S. Cl.
CPC ............ *A61K 31/46* (2013.01); *A61K 31/132* (2013.01); *A61K 31/137* (2013.01); *A61K 31/138* (2013.01)

(58) Field of Classification Search
CPC ... A61K 31/132; A61K 31/138; A61K 31/137
See application file for complete search history.

(56) References Cited

U.S. PATENT DOCUMENTS

| | | | |
|---|---|---|---|
| 4,470,987 | A | 9/1984 | Wurtman et al. |
| 5,889,006 | A | 3/1999 | Lowe et al. |
| 5,977,138 | A | 11/1999 | Wang et al. |
| 6,037,352 | A | 3/2000 | Lowe et al. |
| 6,043,255 | A | 3/2000 | Lowe et al. |
| 6,066,636 | A | 5/2000 | Kozlowski et al. |
| 6,288,068 | B1 | 9/2001 | Lowe et al. |
| 6,292,695 | B1 | 9/2001 | Webster et al. |
| 6,294,554 | B1 | 9/2001 | Clader et al. |
| 6,451,797 | B1 | 9/2002 | Kozlowski et al. |
| 6,458,812 | B1 | 10/2002 | McKittrick et al. |
| 6,498,168 | B2 | 12/2002 | Lowe et al. |
| 6,831,089 | B2 | 12/2004 | Wang et al. |

(Continued)

OTHER PUBLICATIONS

Böhme, et al., "Structure-activity relationships of dimethindene derivatives as new M2-selective muscarinic receptor antagonists," J Med Chem, 46. p. 856-867 (2003).

(Continued)

*Primary Examiner* — San Ming R Hui
(74) *Attorney, Agent, or Firm* — Casimir Jones SC; David Staple

(57) ABSTRACT

The present invention provides compositions and methods for treating or preventing atrial fibrillation (AF). In particular, the present invention provides administration of muscarinic receptor antagonists (e.g., M2-selective muscarinic receptor blockers), administered alone or in combination with other therapeutic agents (e.g., beta-adrenergic receptor blockers) to treat and/or prevent atrial fibrillation.

14 Claims, 5 Drawing Sheets

(56) References Cited

U.S. PATENT DOCUMENTS

| | | |
|---|---|---|
| 6,890,936 B2 | 5/2005 | Boyle et al. |
| 7,285,564 B2 | 10/2007 | Mammen et al. |
| 2009/0281019 A1 | 11/2009 | Arora et al. |
| 2010/0217342 A1 | 8/2010 | Hamdan |
| 2011/0281853 A1 | 11/2011 | Arora et al. |

OTHER PUBLICATIONS

Boyle et al, "Metabolic stabilization of benzylidene ketal M(2) muscarinic receptor antagonists via halonaphthoic acid substitution," Bioorg Med Chem Lett, 11, p. 2311-2314 (2001).

Clader et al., "Muscarinic M2 antagonists: anthranilamide derivatives with exceptional selectivity and in vivo activity," Bioorg Med Chem Lett, 12, p. 319-326 (2004).

Kozlowski et al., "Diphenyl sulfoxides as selective antagonists of the muscarinic M2 receptor," Bioorg Med Chem Lett, 10, p. 2255-2257 (2000).

McNamara et al., "Pharmacological properties of TD-6301, a novel bladder selective muscarinic receptor antagonist," Eur J. Pharmacol, 605, p. 145-152 (2009).

Palani et al., "Isopropyl amide derivatives of potent and selective muscarinic M2 receptor antagonists," Bioorg Med Chem Lett, 14, p. 1791-1794 (2004).

Tumiatti, et al., "Structure-activity relationships of methoctramine-related polyamines as muscarinic antagonist: effect of replacing the inner polymethylene chain with cyclic moieties," Bioorg Med Chem, 15, p. 2312-2321 (2007).

Wang et al., "Design and synthesis of ether analogues as potent and selective M2 muscarinic receptor antagonists," Bioorg Med Chem Lett, 11, p. 891-894 (2001).

Wang et al., "Improving the oral efficacy of CNS drug candidates: discovery of highly orally efficacious piperidinyl piperidine M2 muscarinic receptor antagonists," J. Med Chem, 435, pp. 5415-5418 (2002).

Wang et al., "Sulfide analogues as potent and selective M(2) muscarinic receptor antagonists," Bioorg Med Chem Lett, 12, p. 1087-1091 (2002).

Yalcin et al., "Cardiovascular effect of peripheral injected melittin in normotensive conscious rats: Mediation of the central cholinergic system," Prostaglandins Leukot Essent Fatty Acids., 81(5-6):341-347 (2009).

Wess et al., "Methoctramine selectively blocks cardiac muscarinic M2 receptors in vivo," Naunyn Schmiedebergs Arch Pharmacol., 338(3):246-9 (1988).

International Search Report and Written Opinion for Int'l Application No. PCT/US2011/03629, dated Jan. 11, 2012.

Lazaris et al., Intrastriatal infusions of methoctramine improve memory in cognitively impaired aged rats. Neurobiol Aging. Mar.-Apr. 2003;24(2):379-83.

COMPOSITIONS AND METHODS FOR TREATING OR PREVENTING ATRIAL FIBRILLATION

This application is a continuation of U.S. patent application Ser. No. 13/106,618, filed May 12, 2011, which claims priority to Provisional Patent Application Ser. No. 61/334,023, filed May 12, 2010, and Provisional Patent Application Ser. No. 61/409,691, filed Nov. 3, 2010, which are herein incorporated by reference in their entireties.

STATEMENT REGARDING FEDERALLY SPONSORED RESEARCH OR DEVELOPMENT

This invention was made with government support under R01 HL093490 awarded by the National Institutes of Health. The government has certain rights in the invention.

FIELD OF THE INVENTION

The present invention provides compositions and methods for treating or preventing atrial fibrillation (AF). In particular, the present invention provides administration of muscarinic receptor antagonists (e.g., $M_2$-selective muscarinic receptor blockers), administered alone or in combination with other therapeutic agents (e.g., beta-adrenergic receptor blockers) to treat and/or prevent atrial fibrillation.

BACKGROUND

Cardiac arrhythmias represent a diverse set of conditions characterized by abnormal electrical activity in the heart, resulting in heart rates that are too fast, too slow, or irregular. The most common sustained and clinically significant cardiac arrhythmia is atrial fibrillation (AF). AF is caused by disorganized electrical impulses originating in the atria and pulmonary veins that propogate as irregular electrical signals to the ventricals, resulting in irregular heart rates. AF is frequently associated with symptoms such as palpitations, shortness of breath, fatigue, chest pain and loss of consciousness. AF is a major risk factor for stroke and other embolic events, as it predisposes to the formation of clots in the left atrial appendage, due to the pooling of blood resulting from the inefficient contraction of the atria. The risk of developing AF increases with age, with one in four individuals expected to develop AF during their lifetime. AF currently affects over 2 million Americans, and is expected to affect over 5 million individuals by the year 2050.

AF is frequently associated with conditions such as hypertension, diabetes, valvular heart disease and congestive heart failure (CHF). In fact, up to half of all patients with CHF have concomitant AF. AF is also known to commonly occur after open-heart surgery. The incidence of AF in the perioperative setting is estimated to be around 30% with nearly 50% of patients experiencing AF following valve surgery. Postoperative AF is associated with prolongation in the length of hospitalization, cost of surgery, need for mechanical ventilation, pacemaker requirement, stroke, and possibly death. The economic impact of this disease has been estimated at $6.6 billion. The diagnosis and management of AF have therefore become important and challenging aspects of cardiovascular medicine.

Current treatments for atrial fibrillation include pharmacologic and non-pharmacologic strategies. Pharmacologic strategies for treatment of atrial fibrillation are group into four classes: Class 1: sodium channel blockers, which decrease the rate of electrical conduction in cardiac muscle; Class 2: beta-adrenergic receptor blockers (beta blockers), which decrease the rate of conduction through the heart and thus render the AV node less sensitive to the disorganized electrical signals; Class 3: potassium channel blockers, which slow nerve impulses in the heart muscle, and; Class 4: calcium channel blockers, which impede cardiac muscle cell contraction, allowing blood vessels to expand which increases the oxygenation of cardiac tissue. In addition to treating the underlying atrial fibrillation, patients are routinely treated with blood thinning agents such as aspirin, warfarin, clopidogrel, and ticlopidine to reduce the risk of stroke. Non-pharmacologic treatments include electrical cardioversion and implantation of atrial pacemakers. Recent years have seen the development of more 'curative' techniques such as catheter ablation and surgical Maze procedures. However, these procedures have high efficacy only in selected patient groups, and can be associated with significant complications. In view of the limitations of these empiric ablation/surgical approaches, recent research efforts have attempted to develop novel therapies that target specific mechanisms involved in the genesis of AF.

The autonomic nervous system has been implicated as a major contributor to the genesis and maintenance of focal atrial fibrillation. Recent clinical studies suggest that an alteration of vagal input to the posterior left atrium and the pulmonary veins, as measured by the elimination of vagal reflexes on pulmonary vein stimulation, may improve efficacy of ablation procedures for atrial fibrillation. Recent studies suggest a dominant role for the parasympathetic nervous system in atrial fibrillation, with the sympathetic nervous system playing an important modulatory role in the genesis of this arrhythmia. In the setting of CHF, blocking the sympathetic nervous system changes the characteristics of AF, without significantly affecting the maintenance of AF; these data further support a more modulatory role for the sympathetic nervous system in the creation of AF substrate.

SUMMARY OF THE INVENTION

The present invention provides compositions and methods for treating or preventing atrial fibrillation (AF) for therapeutic or research purposes. In some embodiments, the present invention provides targeted autonomic inhibition of sympathetic activity in the pulmonary vein (PV) and/or posterior left atrium (PLA) to treat and/or prevent atrial fibrillation. In some embodiments, muscarinic receptor antagonists (e.g., $M_2$-selective muscarinic receptor blockers) and/or beta-adrenergic receptor blockers are administered to a subject to treat and/or prevent atrial fibrillation. In some embodiments, the present invention provides compositions and methods to treat or prevent AF through administration of a muscarinic receptor blocker that selectively blocks signaling through the $M_2$ subtype.

In some embodiments, the present invention relates to blockade of $M_2$ muscarinic receptor as a method for treating, preventing, or reversing cardiac arrhythmias, particularly atrial fibrillation. Blockade of the $M_2$ muscarinic receptor is achieved via administration of a therapeutic agent that selectively inhibits the activity of the $M_2$ muscarinic receptor versus other muscarinic receptor subtypes.

In some embodiments, the present invention provides a method of treating, reversing, and/or preventing cardiac arrhythmias comprising administering to a subject a therapeutically effective amount of a $M_2$-selective muscarinic receptor blocking agent. In some embodiments, the cardiac arrhythmia is atrial fibrillation. In some embodiments, the subject is a mammal. In some embodiments, the $M_2$-selective muscarinic receptor blocking agent selectively blocks the $M_2$ receptor subtype by at least five-fold versus the $M_3$ receptor subtype. In some embodiments, the $M_2$-selective muscarinic receptor blocking agent selectively blocks the $M_2$ receptor subtype by at least five-fold versus the $M_1$ receptor subtype. In some embodiments, the $M_2$-selective muscarinic receptor blocking agent selectively blocks the $M_2$ receptor subtype by at least ten-fold versus the $M_3$ receptor subtype. In some embodiments, the $M_2$-selective muscarinic receptor blocking agent selectively blocks the $M_2$ receptor subtype by at least ten-fold versus the $M_3$ receptor subtype. In some embodiments, the $M_2$-selective muscarinic receptor blocking agent is Sch 211803, and/or derivatives thereof. In some embodiments, the $M_2$-selective muscarinic receptor blocking agent is TD-6301, and/or derivatives thereof. In some embodiments, the $M_2$-selective muscarinic receptor blocking agent is methoctramine, and/or derivatives thereof. In some embodiments, the $M_2$-selective muscarinic receptor blocking agent is administered systemically. In some embodiments, the $M_2$-selective muscarinic receptor blocking agent is administered locally. In some embodiments, the $M_2$-selective muscarinic receptor blocking agent is topically administered to the heart of said subject. In some embodiments, the $M_2$-selective muscarinic receptor blocking agent is administered prior to, during, and/or after a heart surgery.

In some embodiments, the present invention provides a method of treating cardiac arrhythmias comprising: (a) testing a subject to determine the presence, type, and/or severity of cardiac arrhythmia; (b) administering to the subject a therapeutically effective amount of a $M_2$-selective muscarinic receptor blocking agent. In some embodiments, the cardiac arrhythmia is atrial fibrillation. In some embodiments, the method further comprises (c) evaluating the subject for a change in the cardiac arrhythmia. In some embodiments, the $M_2$-selective muscarinic receptor blocking agent is selective for the $M_2$ muscarinic receptor over the $M_1$ and $M_3$ receptor subtypes. In some embodiments, the $M_2$-selective muscarinic receptor blocking agent selectively blocks the $M_2$ receptor subtype by at least five-fold versus the $M_3$ receptor subtype. In some embodiments, the $M_2$-selective muscarinic receptor blocking agent selectively blocks the $M_2$ receptor subtype by at least five-fold versus the $M_1$ receptor subtype. In some embodiments, the $M_2$-selective muscarinic receptor blocking agent is selected from Sch 211803 and TD-6301.

In some embodiments, the present invention provides dual blockade of the beta-adrenergic receptor and the M2 muscarinic receptor as a method for treating, preventing, or reversing cardiac arrhythmias, particularly atrial fibrillation (AF). In some embodiments, the present invention provides co-administration of a beta-adrenergic receptor blocker and a muscarinic receptor blocker. In some embodiments, co-administration is performed simultaneously, sequentially, or separately. In some embodiments, two or more pharmacologic agents are administered, either together or separately, via any route of delivery, including but not limited to oral, intravenous, intramuscular, intraperiotoneal, inhalation, buccal, rectal, transdermal, and topical.

In some embodiments, the present invention provides pharmaceutical compositions containing a therapeutically effective amount of a beta-adrenergic receptor blocker, a therapeutically effective amount of a muscarinic receptor blocker, and optional pharmaceutically acceptable carriers. In some embodiments, a pharmaceutical composition contains a therapeutically effective amount of a beta-adrenergic receptor blocker, a therapeutically effective amount of a selective $M_2$ muscarinic receptor blocker, and optionally, appropriate pharmaceutically acceptable In some embodiments, the present invention provides a method of treating, reversing, and/or preventing cardiac arrhythmia in a subject comprising co-administering to the subject a therapeutically effective amount of a beta-adrenergic receptor blocking agent and a therapeutically effective amount of a muscarinic receptor blocking agent. In some embodiments, the beta-adrenergic receptor blocking agent is selected from the group comprising aprenolol, carteolol, levobunolol, mepindolol, metipranolol, nadolol, oxprenolol, timolol, sotalol, esmolol, cateolol, propranolol, betaxolol, penbutolol, metoprolol, acebutolol, atenolol, metoprolol, pindolol, bisoprolol, nebivolol, amosulalol, landiolol, and tilisolol, including any salts, hydrates, solvates, prodrugs, and any crystal forms in which they may occur. In some embodiments, the muscarinic receptor blocker is selected from the group comprising atropine, scopolamine, ipratropium, tropicamide, pirenzepine, diphenhydramine, dimenhydrinate, dicyclomine, oxybutynin, tiotropium, cyclopentolate, atropine methonitrate, trihexyphenidyl, tolterodine, solifenacin, darifenacin, benzatropine, and mebeverine, including any salts, hydrates, solvates, prodrugs, and any crystal forms in which they may occur. In some embodiments, the muscarinic receptor blocker is a selective blocker of the $M_2$ muscarinic receptor subtype. In some embodiments, the cardiac arrhythmia comprises atrial fibrillation. In some embodiments, co-administering of the beta-adrenergic blocker and the muscarinic receptor blocker comprises applying topically. In some embodiments, co-administering of the beta-adrenergic blocker and the muscarinic receptor blocker comprises applying directly to the surface of the heart. In some embodiments, the present invention further comprises applying one or more pharmaceutical carriers.

In some embodiments, the present invention provides a pharmaceutical composition comprising a therapeutically effective amount of a beta-adrenergic receptor blocker, a therapeutically effective amount of a muscarinic receptor blocker, and a pharmaceutically-acceptable carrier. In some embodiments, the beta-adrenergic receptor blocker is selected from the group comprising aprenolol, carteolol, levobunolol, mepindolol, metipranolol, nadolol, oxprenolol, timolol, sotalol, esmolol, cateolol, propranolol, betaxolol, penbutolol, metoprolol, acebutolol, atenolol, metoprolol, pindolol, bisoprolol, nebivolol, amosulalol, landiolol, and tilisolol, including any salts, hydrates, solvates, prodrugs, and any crystal forms in which they may occur. In some embodiments, the muscarinic receptor blocker is selected from the group comprising atropine, scopolamine, ipratropium, tropicamide, pirenzepine, diphenhydramine, dimenhydrinate, dicyclomine, oxybutynin, tiotropium, cyclopentolate, atropine methonitrate, trihexyphenidyl, tolterodine, solifenacin, darifenacin, benzatropine, and mebeverine, including any salts, hydrates, solvates, prodrugs, and any crystal forms in which they may occur.

In some embodiments, the present invention provides a kit for treating, reversing, and/or preventing cardiac arrhythmia in a subject comprising one or more beta-adrenergic receptor blockers and one or more muscarinic receptor blockers (e.g., M2-selective muscarinic receptor blockers). In some embodiments, the beta-adrenergic receptor blocker is selected from the group comprising aprenolol, carteolol, levobunolol, mepindolol, metipranolol, nadolol, oxprenolol, timolol, sotalol, esmolol, cateolol, propranolol, betaxolol, penbutolol, metoprolol, acebutolol, atenolol, metoprolol, pindolol, bisoprolol, nebivolol, amosulalol, landiolol, and tilisolol, including any salts, hydrates, solvates, prodrugs, and any crystal forms in which they may occur. In some embodiments, the muscarinic receptor blocker is selected from the group comprising atropine, scopolamine, ipratropium, tropicamide, pirenzepine, diphenhydramine, dimenhydrinate, dicyclomine, oxybutynin, tiotropium, cyclopentolate, atropine methonitrate, trihexyphenidyl, tolterodine, solifenacin, darifenacin, benzatropine, and mebeverine, including any salts, hydrates, solvates, prodrugs, and any crystal forms in which they may occur. In some embodiments, the muscarinic receptor blocker is a selective blocker of the $M_2$ muscarinic receptor subtype.

In some embodiments, a therapeutic agent may be administered via any standard route of delivery, including but not limited to oral, intravenous, intramuscular, intraperiotoneal, inhalation, buccal, rectal, transdermal, and topical.

In some embodiments, the present invention provides a kit comprising a $M_2$-selective muscarinic receptor blocking agent and a device for topical application of said $M_2$-selective muscarinic receptor blocking agent to the heart of a mammalian subject.

DEFINITIONS

Figure 1:
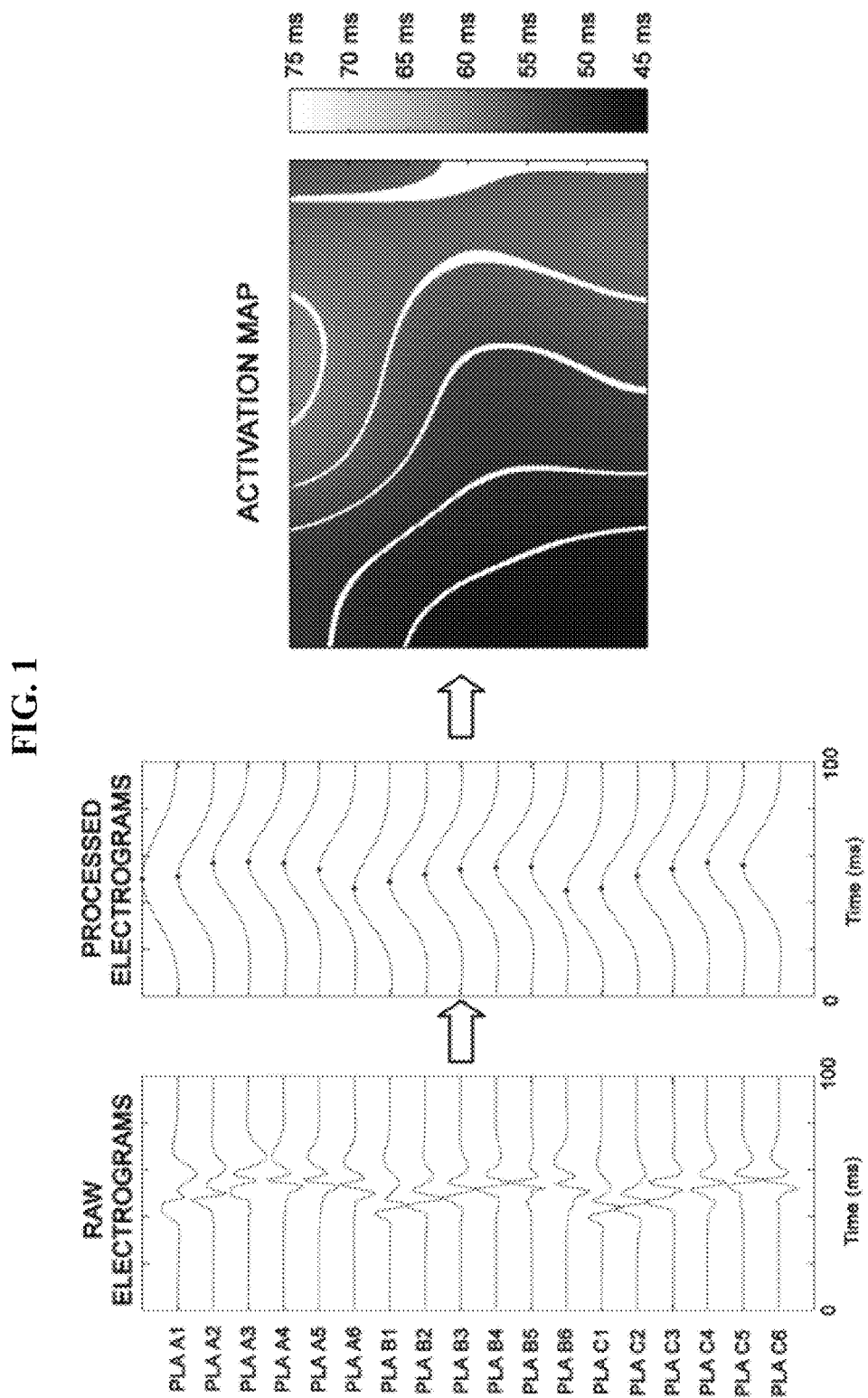
FIG. 1 shows data derived from electrograms. The left panel shows an example of raw electrograms of one sinus beat obtained from the PLA. The middle panel shows the electrograms after band pass filtering, rectification, and low pass filtering. The dots indicate the detected peaks of the processed electrograms. The right panel shows the activation map constructed with the activation times determined from the second panel. The isochrones, indicated by the white lines, show the progression of the wavefront every 3 milliseconds.

As used herein, the term "subject" refers to any animal, mammal, rodent, canine, feline, equine, bovine, porcine, primate (e.g. non-human primate), or human to which compositions of the present invention are administered or methods of the present invention are applied. In the case of a human subject, the term "patient" may be used interchangeably. A subject may suffer from a disease, disorder, or condition to be treated by the present invention, or may receive the compositions of the present invention, or undergo the methods of the present invention preventatively.

As used herein, the term "co-administration" refers to the administration of two or more compositions to a subject. The compositions may be administered to treat the same or different diseases, disorders, and/or conditions. The compositions may be administered by the same route or different routes of administration (e.g. oral, parenateral, topical, intervenous, transmucosal, and/or inhalation routes). The compositions may be administered simultaneously or at different times. The compositions may be administered simultaneously, but formulated for release at different times or in different regions of the subject. The compositions may target the same or different pathways within the subject. The compositions may be provided in a single formulation (e.g., same delivery route, same solution, etc.).

DETAILED DESCRIPTION OF THE INVENTION

The present invention relates to compositions and methods for treating, reversing, and/or preventing cardiac arrhythmias. In particular, the present invention provides compositions and methods for treating, reversing, and/or preventing cardiac arrhythmias, including atrial fibrillation, ventricular fibrillation, and cardiac arrhythmias resulting from myocardial ischemic injury or surgical complications.

Both sympathetic and parasympathetic nerve activity in the heart are mediated by heterotrimeric G-protein coupled pathways initiated by G-protein coupled receptors (GPCRs). Activation of beta-adrenergic receptors, which are coupled to $G_s$, leads to an increase in conduction velocity and several other excitatory responses in the heart. Activation of muscarinic $M_2$ receptors, which are coupled to $G_i$, leads to a marked shortening of refractoriness in the atria. In combination, these two limbs of the autonomic nervous system have been demonstrated to create substrate for atrial fibrillation.

In some embodiments, compositions and methods are provided to treat or prevent cardiac arrhythmias (e.g., AF) in a subject (e.g. mammal, canine, rodent, primate, human, etc.) via co-administration of a beta-adrenergic receptor blocker and a muscarinic receptor blocker (e.g., $M_2$-selective muscarinic receptor blocker or other muscarinic receptor blocker). In some embodiments, co-administration of a beta-adrenergic receptor blocker and a muscarinic receptor blocker (e.g., $M_2$-selective muscarinic receptor blocker or other muscarinic receptor blocker) effectively modulates the activity of both the sympathetic and parasympathetic pathways, both of which contribute to the genesis and maintenance of AF. In some embodiments, the present invention provides a pharmaceutical composition that contains a therapeutically effective amount of a beta-adrenergic receptor blocker, a therapeutically effective amount of a muscarinic receptor blocker (e.g., $M_2$-selective muscarinic receptor blocker or other muscarinic receptor blocker), and optionally, appropriate pharmaceutically acceptable carriers.

In some embodiments, the present invention provides muscarinic receptor antagonists, particularly compositions that are selective antagonists of the $M_2$ receptor subtype, and methods of administration for treating, reversing, and/or preventing cardiac arrhythmias therewith. In some embodiments, the present invention provides $M_2$ muscarinic receptor antagonists. In some embodiments, the present invention provides $M_2$ muscarinic receptor blocking agents. In some embodiments, the present invention provides $M_2$ muscarinic receptor antagonists (e.g. selective $M_2$ muscarinic receptor antagonists) for treating, reversing, and/or preventing cardiac arrhythmias, including atrial fibrillation and cardiac arrhythmias resulting from myocardial ischemic injury and/or surgical complications. In some embodiments, the present invention provides methods for treating and/or preventing post-operative AF. In some embodiments, the present invention provides treating and/or preventing heart-associated conditions (e.g. AF) in a mammal (e.g. rodent, canine, feline, bovine, equine, porcine, non-human primate, human, etc.).

In some embodiments, the present invention provides methods for treating and/or preventing AF in a mammal (e.g. rodent, canine, primate, human, etc.) via co-administration of a beta-adrenergic receptor blocker and a selective blocker of the $M_2$ muscarinic receptor. In some embodiments, the present invention provides methods for treating and/or preventing post-operative AF in a mammal (e.g. rodent, canine, primate, human, etc.) via co-administration (e.g. topically) of a beta-adrenergic receptor blocker and a muscarinic receptor blocker (e.g. selective blocker of the $M_2$ muscarinic receptor) to the heart (e.g. the surface of the heart). In some embodiments, the present invention provides methods for treating and/or preventing post-operative AF in a mammal (e.g. rodent, canine, primate, human, etc.) via co-administration (e.g. topically) of a beta-adrenergic receptor blocker and a muscarinic receptor blocker (e.g. selective blocker of the $M_2$ muscarinic receptor) to the heart (e.g. the surface of the heart) directly following surgery. In some embodiments, the present invention provides methods for treating and/or preventing post-operative AF in a mammal (e.g. rodent, canine, primate, human, etc.) via topical co-administration of a beta-adrenergic receptor blocker and a muscarinic receptor blocker (e.g. selective blocker of the $M_2$ muscarinic receptor) to the surface of the heart directly following surgery. In some embodiments, the present invention provides methods for treating or preventing post-operative AF in a mammal via co-administration of a beta-adrenergic receptor blocker and a selective blocker of the $M_2$ muscarinic receptor topically to the surface of the heart directly following surgery.

In some embodiments, the present invention provides pharmaceutical compositions comprising a therapeutically effective amount of a beta-adrenergic receptor blocker, a therapeutically effective amount of a muscarinic receptor blocker (e.g. selective blocker of the $M_2$ muscarinic receptor), and optionally, appropriate pharmaceutically acceptable carriers. In some embodiments, the present invention provides pharmaceutical compositions comprising a therapeutically effective amount of a beta-adrenergic receptor blocker, a therapeutically effective amount of a selective blocker of the $M_2$ muscarinic receptor, and optionally, appropriate pharmaceutically acceptable carriers.

In some embodiments, the present invention provides compositions comprising one or more beta-adrenergic receptor blockers, and methods of use thereof. In some embodiments, any suitable beta-adrenergic receptor blocker may find use with the present invention. In some embodiments, a suitable beta-adrenergic receptor blocker comprises a non-selective beta-adrenergic receptor blocker (e.g. capable of blocking two or more of β1-, β3-, and β3-adrenergic receptors; capable of blocking beta-adrenergic receptor and one or more other receptors (e.g. alpha-adrenergic receptor); etc.), a β1-selective beta-adrenergic receptor blocker, and/or a β2-selective beta-adrenergic receptor blocker. In some embodiments, non-selective beta-adrenergic receptor blockers include, but are not limited to: Alprenolol, Bucindolol, Carteolol, Carvedilol, Labetalol, Nadolol, Penbutolol, Pindolol, Propranolol, and Timolol. In some embodiments, β1-selective beta-adrenergic receptor blockers include, but are not limited to: Acebutolol, Atenolol, Betaxolol, Bisoprolol, Celiprolol, Esmolol, Metoprolol, and Nebivolol. In some embodiments, β2-selective beta-adrenergic receptor blockers include, but are not limited to: Butaxamine and ICI-118,551. In some embodiments, one or more of the above listed beta-adrenergic receptor blockers, or other suitable beta-adrenergic receptor blockers known to those in the art, are co-administered with one or more muscarinic receptor blockers (e.g. a selective blocker of the $M_2$ muscarinic receptor), and optionally, one or more appropriate pharmaceutically acceptable carriers.

In some embodiments, the present invention provides compositions comprising one or more muscarinic receptor blockers (e.g. a selective blocker of the $M_2$ muscarinic receptor), and methods of use thereof. In some embodiments, any suitable muscarinic receptor blockers (e.g. a selective blocker of the $M_2$ muscarinic receptor) may find use with the present invention. In some embodiments, muscarinic receptor blockers include, but are not limited to: atropine, scopolamine (L-Hyoscine), Ipratropium (e.g. ATROVEN, APOVENT, etc.), Tropacamide, Pirenzepine, Dihenhydramine (e.g. BENADRYL), Dimenhydrinate (e.g. DRAMAMINE), Dicyclomine, Flavoxate, Oxybutynin (e.g. DITROPAN), Tiotropium (e.g. SPIRIVA), Cyclopentolate, Atropine methonitrate, Trihexyphenidyl/Benzhexol (e.g. ARTANE), Tolterodine (e.g. DETRUSITOL, DETROL, etc.), Solifenacin (e.g. VESICARE), Darifenacin (e.g. ENABLEX), Benzatropine (e.g. COGENTIN), Mebeverine (e.g. COLOFAC, DUSPATAL, DUSPATALIN, etc.), and Pyrocyclidine. In some embodiments, the present invention provides administration of one or more $M_2$-selective muscarinic receptor blockers from the above list to a subject to treat and/or prevent AF or other heart conditions. In some embodiments, one or more of the above listed muscarinic receptor blockers (e.g. a selective blocker of the $M_2$ muscarinic receptor) are co-administered with one or more beta-adrenergic receptor blockers (e.g. one or more beta-adrenergic receptor blockers listed above or other suitable beta-adrenergic receptor blockers known to those in the art), and optionally, one or more appropriate pharmaceutically acceptable carriers.

In some embodiments, the present invention provides methods to treat or prevent AF in a mammal (e.g. rodent, canine, feline, bovine, equine, porcine, non-human primate, human, etc.) via administration of a selective $M_2$ muscarinic receptor blocker (e.g. antagonist), effectively modulating the activity of the parasympathetic pathway, which contributes to the genesis and maintenance of AF, although the present invention is not limited to any particular mechanism of action and an understanding of the mechanism of action is not necessary to practice the present invention. In some embodiments, any suitable $M_2$ muscarinic receptor blocker (e.g. antagonist) finds use with the treatment and/or preventative methods of the present invention (e.g. tolterodine, 4-(hydroxymethyl)tolterodine, etc.). Examples of $M_2$ muscarinic receptor blockers include, but are not limited to tolterodine, which is 1.7-fold selective for $M_2$ versus $M_3$, and 4-(hydroxymethyl)tolterodine, which is 2-fold selective for $M_2$ versus $M_3$. In some embodiments, 4-(Hydroxymethyl)tolterodine is administered as fesoterodine, which is a prodrug of the active agent.

In some embodiments, the present invention provides administration of Muscarinic receptor blockers that are selective for the $M_2$ subtype to treat and/or prevent cardiac arrhythmias (e.g. AF). In some embodiments, the present invention provides administration of $M_2$-selective antagonists for the treatment and/or prevention of cardiac arrhythmias (e.g. AF), for example $M_2$-selective antagonists have been described in the scientific literature (see, e.g.; Kozlowski, J. A. et al. *Bioorg. Med. Chem. Lett.* 2000, 10, 2255-2257; Wang, Y. et al. *Bioorg. Med. Chem. Lett.* 2001, 11, 891-894; Boyle, C. D. et al. *Bioorg. Med. Chem. Lett.* 2001, 11, 2311-2314; Wang, Y. et al. *Bioorg. Med. Chem. Lett.* 2002, 12, 1087-1091; Wang, Y. et al. *J. Med. Chem.* 2002, 45, 5415-5418; Böhme, T. M. et al. *J. Med. Chem.* 2003, 46, 856-867; Palani, A. et al. *Bioorg. Med. Chem. Lett.* 2004, 14, 1791-1794; Clader, J. W. et al. *Bioorg. Med. Chem.* 2004, 12, 319-326; McNamara, A. et al. *Eur. J. Pharmacol.*

2009, 605, 145-152; herein incorporated by reference in their entireties). In some embodiments, muscarinic receptor blockers that are selective for the $M_2$ subtype which find use in the present invention include, but are not limited to those described in U.S. Pat. No. 5,889,006; U.S. Pat. No. 6,037,352; U.S. Pat. No. 6,043,255; U.S. Pat. No. 6,066,636; U.S. Pat. No. 6,288,068; U.S. Pat. No. 6,294,554; U.S. Pat. No. 6,451,797; U.S. Pat. No. 6,458,812; U.S. Pat. No. 6,498,168; U.S. Pat. No. 6,831,089; U.S. Pat. No. 6,890,936; U.S. Pat. No. 7,285,564; and their foreign equivalents; herein incorporated by reference in their entireties). In some embodiments, the compounds described in the above references are suitable for use in the treatment and/or prevention methods of the present invention, and are hereby incorporated by reference. In some embodiments, $M_2$-selective antagonists for use in the present invention include, but are not limited to 3-α-chloroimperialine; di-N-substituted piperazines; and 1,4-di-substituted piperidines; and derivitives thereof.

In some embodiments, the present invention provides treating or preventing cardiac arrhythmias and/or AF in a mammal via administration of Sch 211803. Sch 211803 is 734-fold and 786-fold selective for $M_2$ versus $M_1$ and $M_3$, respectively (Wang, Y. et al. *Bioorg. Med. Chem. Lett.* 2002, 12, 1087-1091; herein incorporated by reference in its entirety).

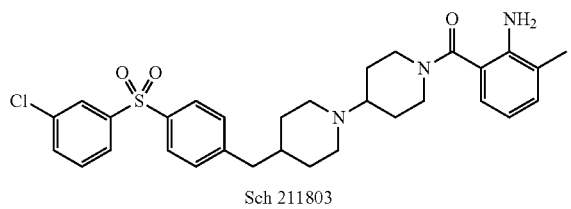 [SMILES: Cc1cccc(C(=O)N2CCC(N3CCC(Cc4ccc(S(=O)(=O)c5cccc(Cl)c5)cc4)CC3)CC2)c1N]

Sch 211803

In some embodiments, the present invention provides treating or preventing cardiac arrhythmias and/or AF in a mammal via administration of TD-6301. TD-6301 is 31-fold and 36-fold selective for $M_2$ versus $M_1$ and $M_3$, respectively (McNamara, A. et al. *Eur. J. Pharmacol.* 2009, 605, 145-152; herein incorporated by reference in its entirety).

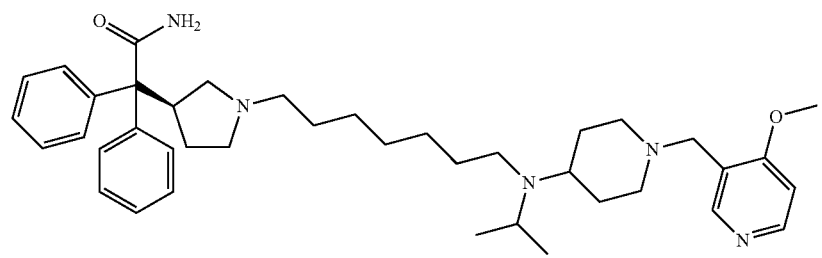

TD-6301

In some embodiments, the present invention provides treating or preventing cardiac arrhythmias and/or AF in a mammal via administration of methoctramine. Methoctramine is 35-fold and 219-fold selective for $M_2$ versus $M_1$ and $M_3$, respectively (Tumiatti, V. et al. *Bioorg. Med. Chem.* 2007, 15, 2312-2321); herein incorporated by reference in its entirety).

In some embodiments, the present invention provides treating or preventing AF (e.g. in a mammal) via administration of a muscarinic receptor blocker that is at least five to ten fold (5-10-fold) selective for the $M_2$ subtype versus the $M_1$ and/or $M_3$ subtypes. In some embodiments, a muscarinic receptor blocker of the present invention is selectively inhibitory for the $M_2$ subtype over the $M_1$ subtype (e.g. at least 1.5-fold selectivity, at least 2-fold selectivity, at least 3-fold selectivity, at least 4-fold selectivity, at least 5-fold selectivity, at least 10-fold selectivity, at least 100-fold selectivity, etc.). In some embodiments, a muscarinic receptor blocker of the present invention is selectively inhibitory for the $M_2$ subtype over the $M_3$ subtype (e.g. at least 1.5-fold selectivity, at least 2-fold selectivity, at least 3-fold selectivity, at least 4-fold selectivity, at least 5-fold selectivity . . . at least 10-fold selectivity . . . at least 100-fold selectivity . . . at least 1000-fold selectivity, etc.).

In some embodiments, the present invention provides treatment and/or prevention of AF through administration of two or more therapeutic compounds (e.g. at least one muscarinic receptor blocker (e.g. 1, 2, 3, 4, 5, 6 . . . ) and at least one beta-adrenergic receptor blocker (e.g. 1, 2, 3, 4, 5, 6 . . . )). In some embodiments, the present invention provides treatment and/or prevention of AF through administration of at least one $M_2$-selective muscarinic receptor blocker (e.g. 1, 2, 3, 4, 5, 6 . . . ) and at least one beta-adrenergic receptor blocker (e.g. 1, 2, 3, 4, 5, 6 . . . )). In some embodiments, the therapeutic compounds are formulated together into a single pharmaceutical composition (e.g. pill, topically-administered liquid, etc.). In some embodiments, the therapeutic compounds formulated together within a pharmaceutical composition are configured for separate therapeutic release regimens (e.g. timed release, delayed release, immediate release, etc.). In some embodiments, the therapeutic compounds formulated together within a pharmaceutical composition are both configured for immediate effectiveness. In some embodiments, the therapeutic compounds are formulated as separate pharmaceutical compositions to be co-administered. In some embodiments, co-administration comprises administering separate pharmaceutical compositions simultaneously, or near simultaneously. In some embodiments, co-administration comprises a therapeutic strategy in which a subject is administered separate pharmaceutical compositions, but not necessarily together. In some embodiments, co-administered pharmaceutical compositions are administered via different routes of administration, at different times, and/or to different regions of a subject.

In some embodiments, the present invention provides methods for treating and/or preventing post-operative coronary complications (e.g. AF) in a mammal via administration of a muscarinic receptor blocker (e.g. antagonist) that is selective for the $M_2$ subtype versus the $M_1$ and/or $M_3$ subtypes (e.g. at least 1.5-fold selectivity, at least 2-fold selectivity, at least 3-fold selectivity, at least 4-fold selectivity, at least 5-fold selectivity, at least 10-fold selectivity, at least 100-fold selectivity, at least 1000-fold selectivity, etc.). In some embodiments, the present invention provides methods for treating and/or preventing post-operative AF or VF in a mammal via administration of a muscarinic receptor blocker (e.g. antagonist) that is selective for the $M_2$ subtype versus the $M_1$ and/or $M_3$ subtypes (e.g. at least 1.5-fold selectivity, at least 2-fold selectivity, at least 3-fold selectivity, at least 4-fold selectivity, at least 5-fold selectivity, at least 10-fold selectivity, at least 100-fold selectivity, at least 1000-fold selectivity, etc.). In some embodiments $M_2$-selective antagonist is administered during surgery, prior to surgery, and/or following surgery. In some embodiments, $M_2$-selective antagonist is administered directly to the heart (e.g. topically, intravenously, etc.) during surgery, prior to surgery, and/or following surgery. In some embodiments, $M_2$-selective antagonist is administered topically to the surface of the heart during, or directly prior to, completion of surgery. In some embodiments, $M_2$-selective antagonist is administered directly to the heart. In some embodiments, $M_2$-selective antagonist is administered to the patient systemically (e.g. intravenously, orally, etc.). In some embodiments, the present invention provides methods for treating and/or preventing post-operative AF or VF in a mammal via administration of a $M_2$-selective muscarinic receptor blocker topically to the surface of the heart during, or directly prior to, completion of surgery.

In some embodiments, one or more $M_2$-selective muscarinic receptor antagonists are co-administered with one or more additional therapeutic agents (e.g. a beta-adrenergic receptor blocking agent) to treat and/or prevent AF, cardiac arrhythmias, or other heart conditions. In some embodiments, one or more $M_2$-selective muscarinic receptor antagonists are co-administered with one or more pharmaceutical carriers. In some embodiments, the present invention provides treatment and/or prevention of AF through administration of one or more therapeutic compounds (e.g. at least one $M_2$-selective muscarinic receptor blocker (e.g. 1, 2, 3, 4, 5, 6 . . . ) and optionally one or more additional therapeutic compounds (e.g. a beta-adrenergic receptor blocking agent)). In some embodiments, one or more therapeutic compounds (e.g. at least one $M_2$-selective muscarinic receptor blocker) are formulated together into a single pharmaceutical composition (e.g. pill, topically-administered liquid, etc.). In some embodiments, one or more therapeutic compounds (e.g. at least one $M_2$-selective muscarinic receptor blocker) are formulated for release under a particular release regimen (e.g. timed release, delayed release, immediate release, etc.). In some embodiments, a $M_2$-selective muscarinic receptor blocker is co-administered with additional $M_2$-selective muscarinic receptor blockers and/or other therapeutic agents. In some embodiments, co-administered compounds are formulated under a single release regimen (e.g. timed release, delayed release, immediate release, etc.). In some embodiments, co-administered compounds are formulated for separate release regimens (e.g. timed release, delayed release, immediate release, etc.). In some embodiments, a $M_2$-selective muscarinic receptor blocker and an additional therapeutic compound are formulated as separate pharmaceutical compositions to be co-administered. In some embodiments, a $M_2$-selective muscarinic receptor blocker and an additional therapeutic compound are administered under a therapeutic strategy in which a subject is administered separate pharmaceutical compositions, but not necessarily together. In some embodiments, co-administered pharmaceutical compositions are administered via different routes of administration, at different times, and/or to different regions of a subject.

In some embodiments, the present invention targets the expression the $M_2$-subtype muscarinic receptor. For example, in some embodiments, the present invention employs compositions comprising oligomeric antisense or RNAi compounds, particularly oligonucleotides, for use in modulating the function of nucleic acid molecules encoding $M_2$-subtype muscarinic receptor (Genbank Accession Nos. NM_001006630.1, NM_000739.2, NM_001006632.1, and/or NM_001006631.1), ultimately modulating the amount of $M_2$-subtype muscarinic receptor expressed.

In some embodiments, RNAi is utilized to inhibit $M_2$-subtype muscarinic receptor function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. Chemically synthesized siRNAs are powerful reagents for therapeutic targeting of genes.

In other embodiments, $M_2$-subtype muscarinic receptor expression is modulated using antisense compounds that specifically hybridize with one or more nucleic acids encoding $M_2$-subtype muscarinic receptor. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of $M_2$-subtype muscarinic receptor.

In some embodiments, siRNA and/or antisense approaches are administered alone or in combination with other $M_2$-subtype muscarinic receptor inhibitors. In some embodiments, $M_2$-subtype muscarinic receptor blockers are administered with other pharmacologic strategies for treatment of heart conditions (e.g. AF). In some embodiments, $M_2$-subtype muscarinic receptor blockers are co-administered with one or more of: a sodium channel blocker, a beta-adrenergic receptor blocker, a potassium channel blocker, or a calcium channel blocker. In some embodiments, $M_2$-subtype muscarinic receptor blockers are co-administered with one or more agents for treating atrial fibrillation, such as aspirin, warfarin, clopidogrel, and ticlopidine to reduce the risk of stroke. In some embodiments, $M_2$-subtype muscarinic receptor blockers are co-administered non-pharmacologic treatments for AF, such as electrical cardioversion and implantation of atrial pacemakers.

In some embodiments, compositions described herein and pharmaceutical agents made therefrom are administered via any desired oral, parenateral, topical, intervenous, transmucosal, and/or inhalation routes. Pharmaceutical agents may be administered in the form of a composition which is formulated with a pharmaceutically acceptable carrier and optional excipients, flavors, adjuvants, etc. in accordance with good pharmaceutical practice.

In some embodiments of the present invention, compositions are administered to a patient alone or in combination with other therapies, pharmaceuticals, supplements, and/or a specified diet, or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions may be administered alone.

Depending on the goal of administration, compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

In some embodiments, compositions (e.g. co-administrations of stimulant and non-stimulant) may be in the form of a solid, semi-solid or liquid dosage form: such as tablet, capsule, pill, powder, suppository, solution, elixir, syrup, suspension, cream, lozenge, paste and spray containing the first and second agents formulated appropriately to provide the desired time-release profile. As those skilled in the art would recognize, depending on the chosen route of administration, the composition form is selected.

In some embodiments, pharmaceutical agents may be administered in single or multiple doses. In preferred embodiments, the pharmaceutical compound is administered in a single dose. In some embodiments, a single oral pill or capsule is provided containing the first and second agents. In some preferred embodiments, a capsule is used containing the first agent in a form that permits early release and the second agent in a form that permits later release. The particular route of administration and the dosage regimen will be determined by one of skill, in keeping with the condition of the individual to be treated and said individual's response to the treatment.

In some embodiments, substituents of a composition of the present invention may be adjusted to provide desirable solubility or other characteristics for administration by any suitable technique.

The present invention also provides pharmaceutical agents in a unit dosage form for administration to a subject, comprising pharmaceutical compounds and one or more nontoxic pharmaceutically acceptable carriers, adjuvants or vehicles. The amount of the active ingredients that may be combined with such materials to produce a single dosage form will vary depending upon various factors, as indicated above. A variety of materials can be used as carriers, adjuvants, and vehicles in the composition of the invention, as available in the pharmaceutical art.

EXPERIMENTAL

The following example is provided in order to demonstrate and further illustrate certain preferred embodiments and aspects of the present invention and are not to be construed as limiting the scope thereof.

Example 1

Canine CHF Model

Sterile surgery for pacemaker implantation was performed in canine subjects. The pacemaker was programmed to pace the right ventricle for 3 weeks at a rate of 240 beats per minute. CHF was confirmed by left ventricular dysfunction assessed by serial echocardiogram and by clinical assessment (e.g. ascites, tachypnea, reduced physical activity).

Experimental Setup.

After the 3 weeks of pacing, the subjects were intubated and a median sternonomy was performed under general anesthesia with isoflurane. High density plaques were applied to the left inferior pulmonary vein (PV; 8×5 electrodes; 2.5 mm spacing), the posterior left atrium (PLA; 7×3 electrodes, 5 mm spacing) and the left atrial appendage (LAA; 7×3 electrodes, 5 mm spacing) for bipolar electrogram recordings and pacing. The PV plaque was placed circumferentially around the vein while the other two plaques were laid flat on the PLA and LAA epicardium. The left cervical vagus nerve was isolated and attached with bipolar electrodes for electrical stimulation.

Autonomic Maneuvers.

Effective refractory period measurement, activation mapping, and arrhythmia induction were performed at baseline and for a series of parasympathetic including:
  (a) Electrical stimulation of the isolated left cervical vagus nerve with a stimulation rate of 20 Hz, pulse width of 5 ms, and amplitude of 10 volts (Grass S44G, Astromed, West Warwick, R.I.);
  (b) Acetylcholinesterase inhibition through physostigmine infusion IV (3 to 4 mg);
  (c) Combined cervical vagal stimulation with physostigmine;
  (d) Local cholinergic stimulation of the PLA with topical application of 1.0 mM carbachol to the PLA; and
  (e) Complete parasympathetic blockade with atropine (0.04 mg/kg).

Effective refractory period measurement, activation mapping, and arrhythmia induction were performed at baseline and for a series of parasympathetic including:
  (a) Systemic sympathetic stimulation with isoproterenol infusion—enough to increase the sinus rate by 20 beats per minute;
  (b) Complete sympathetic blockage with propranolol (0.2 mg/kg); and
  (c) Complete autonomic blockade with propranolol (0.2 mg/kg) and atropine (0.4 mg/kg).

A subset of the described maneuvers was completed for each subject. Hearts were removed and dissected upon completion of the in vivo portion of the study.

Effective Refractory Periods.

Effective refractory periods (ERPs) were obtained from 5 distributed sites from the PV, 6 sites from the PLA, and 4 sites from the LAA during each autonomic intervention. For each ERP, the pacing protocol consisted of a drive train (S1) of eight beats with a cycle length of 400 ms followed by an extrastimulus (S2). The S2 was decremented by 10 ms until loss of capture. The longest S2 which did not capture was considered the ERP for that particular site. Pacing was performed at an output current twice the threshold required for consistent capture of the tissue. The mean ERP was used as the representative ERP for each of the three sites as well as the entire left atrium.

Atrial Fibrillation Sustainability.

AF induction was attempted in the LAA during baseline, with atropine, and with double blockade. This protocol consisted of burst pacing at a cycle length of 180 ms to 100 ms with 10 ms decrements for 10 seconds for each cycle length. Current was set at four times the threshold for capture. The maximum durations of the AF episodes induced by the burst pacing were calculated for each intervention.

Atrial Fibrillation Dominant Frequency.

Electrograms recorded during the maximum duration AF episodes obtained by burst pacing (described in Atrial Fibrillation Sustainability above) were analyzed with dominant frequency (DF) analysis. Four four-second segments (16 seconds total) of each channel and AF episode after a stabilization period of four seconds following the cessation of burst pacing were selected for analysis. Electrograms were pre-processed with 40 to 250 Hz band pass filtering, rectification, and 20 Hz low pass filtering (Arora R, Ng J, Ulphani J, Mylonas I, Subacius H, Shade G, Gordon D, Morris A, He X, Lu Y, Belin R, Goldberger J J, Kadish A H. Journal of the American College of Cardiology. 2007; 49(12):1340-1348, herein incorporated by reference in its entirety). Power spectra of the processed electrograms were obtained using the Fast Fourier Transform. The DF, defined as the frequency with the highest power in the power spectrum, was used as the estimation of the local AF activation rate (Ng J, Kadish A H, Goldberger J J. Effect of electrogram characteristics on the relationship of dominant frequency to atrial activation rate in atrial fibrillation. Heart Rhythm. 2006; 13:1295-1305, herein incorporated by reference in its entirety). A composite DF from each region was calculated by averaging the values spatially across all channels of the plaque and temporally across the four four-second segments.

Activation Mapping.

Recordings from the plaques on the PV, PLA, and LAA were made during sinus rhythm during baseline, parasympathetic blockade, and sympathetic blockade. Creation of activation maps from these recordings and the subsequent analysis were performed offline using custom software programmed in Matlab (Mathworks, Natick, Mass.). Activation times for each electrode recording for a specific beat were selected at the peak voltage of the bipolar electrograms after band pass filtering (40 to 250 Hz), rectification, and low pass filtering (20 Hz). The filtering and rectification steps were used to account for the different morphologies of bipolar electrogram recordings (Botteron G W, Smith J M. IEEE Trans Biomed Eng. 1995; 42:579-586; and, Botteron G W, Smith J M. Circulation. 1996; 93:513-518, herein incorporated by reference in its entirety). Two-dimensional activation maps for the PV, PLA, and LAA were then constructed from the activation times (SEE FIG. 1).

Figure 2A:
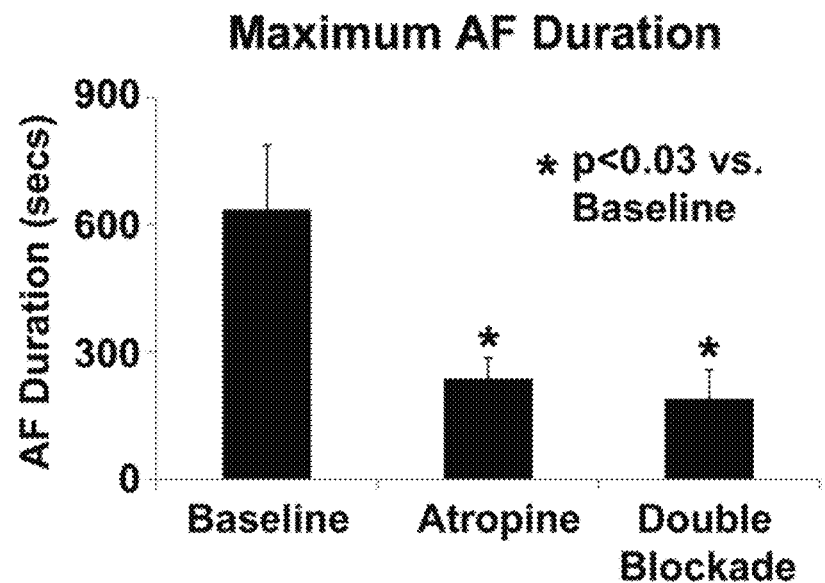
FIGS. 2A-C show the results of combination therapy consisting of a muscarinic receptor blocker (atropine) with a beta-adrenergic blocker (propranolol) on duration and frequency of AF in the canine model.
Figure 2B:
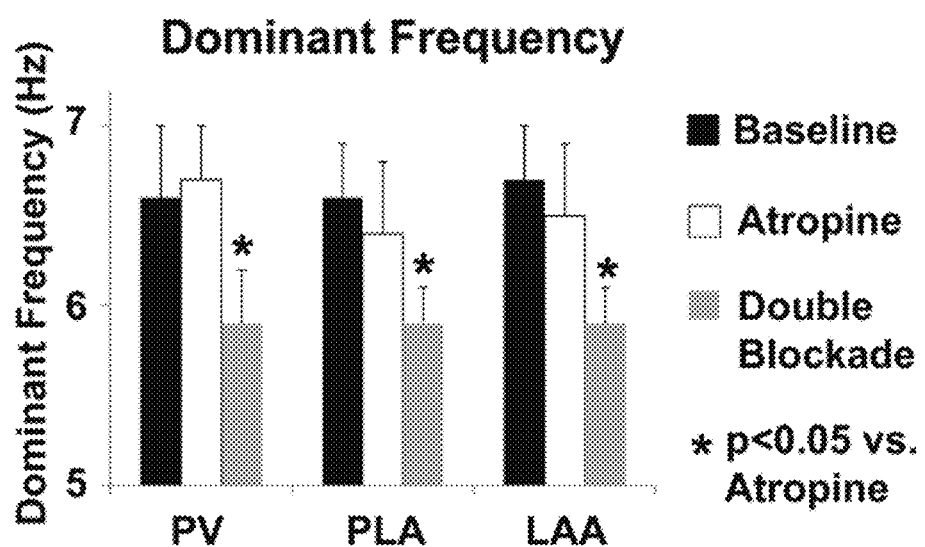
Figure 2C:
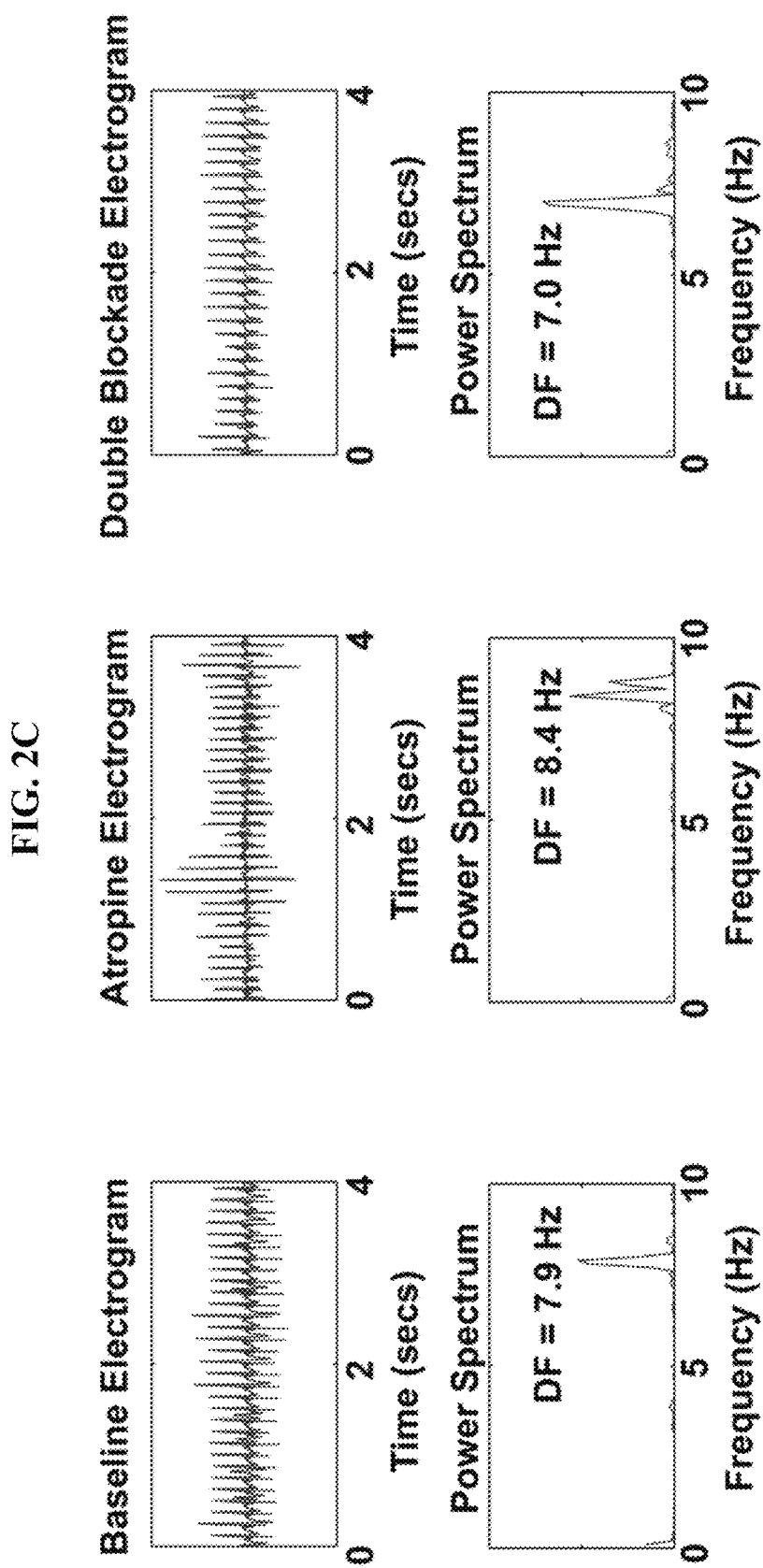

To measure the similarity of activation patterns between two different autonomic conditions, correlation coefficients comparing the activation times at baseline with the activation times during autonomic blockade were calculated. A correlation coefficient of 1 signifies identical activation patterns between a beat at baseline and a beat during autonomic blockade. A correlation coefficient near zero signifies significant change. Correlation coefficients between two repeated beats at baseline and two repeated beats during the autonomic blockade were calculated to assess stability of the activation maps (SEE FIGS. 2A-C).

Example 2

Canines were subjected to heart failure (HF) by rapid ventricular pacing (240/min for 3 weeks). Vagal stimulation induced ERP shortening (VS-ΔERP) (ms) was assessed in the test canines as well as controls at multiple sites in the LA. VS-ΔERP was reassessed in the presence of an acetylcholineesterase (AChE) inhibitor (physostigmine). Explanted LA were subjected to 1) ELISA for acetylcholinesterase (AChE) activity, 2) AChE immunostaining and 3) radioactive M2 receptor binding assay.

VS-ΔERP was significantly reduced in HF, but was restored by physostigmine (from 10±4 to 28±4). The number of parasympathetic ganglia in the LA was increased in HF (HF vs. control=3.8±3 $cm^{-2}$ vs. 0.95±1.5 $cm^{-2}$). AChE activity was also greater in HF. There was no change in M2 binding activity in HF compared to control. There was a profound increase in parasympathetic innervation, and a decrease in parasympathetic responsiveness in the HF LA, despite intact M2 receptor binding. Experiments conducted during development of embodiments, of the present invention demonstrate a dramatic increase in AChE activity underlying this phenomenon, indicating a key protective mechanism against AF in the failing heart.

Example 3

Canine Arrhythmia Model

Methoctramine, a muscarinic receptor blocker that is selective for blocking the $M_2$ receptor subtype (Tumiatti, V. et al. Bioorg. Med. Chem. 2007, 15, 2312-2321), was evaluated for its ability to decrease effective refractory period and atrial fibrillation induced by vagal stimulation. Open chest electrophysiological mapping was performed in a canine model as previously described (Arora, R. et al. Am. J. Physiol. Heart Circ. Physiol. 2008, 294, H134-H144). Recording plaques were placed on the posterior left atrium (PLA), left superior pulmonary vein (PV) and the left atrial appendage (LAA). At baseline, effective refractory periods (ERPs) were obtained at multiple sites on each plaque in the absence and presence of vagal stimulation (VS). AF inducibility was also assessed under each of these conditions i.e. with and without VS. After baseline measurements had been made, methoctramine tetrahydrochloride hydrate (20 microgram/kg), dissolved in normal saline, was administered via a single iv injection. 10-15 minutes after methoctramine administration, ERPs and AF inducibility were reassessed in the absence and presence of VS.

Figure 3:
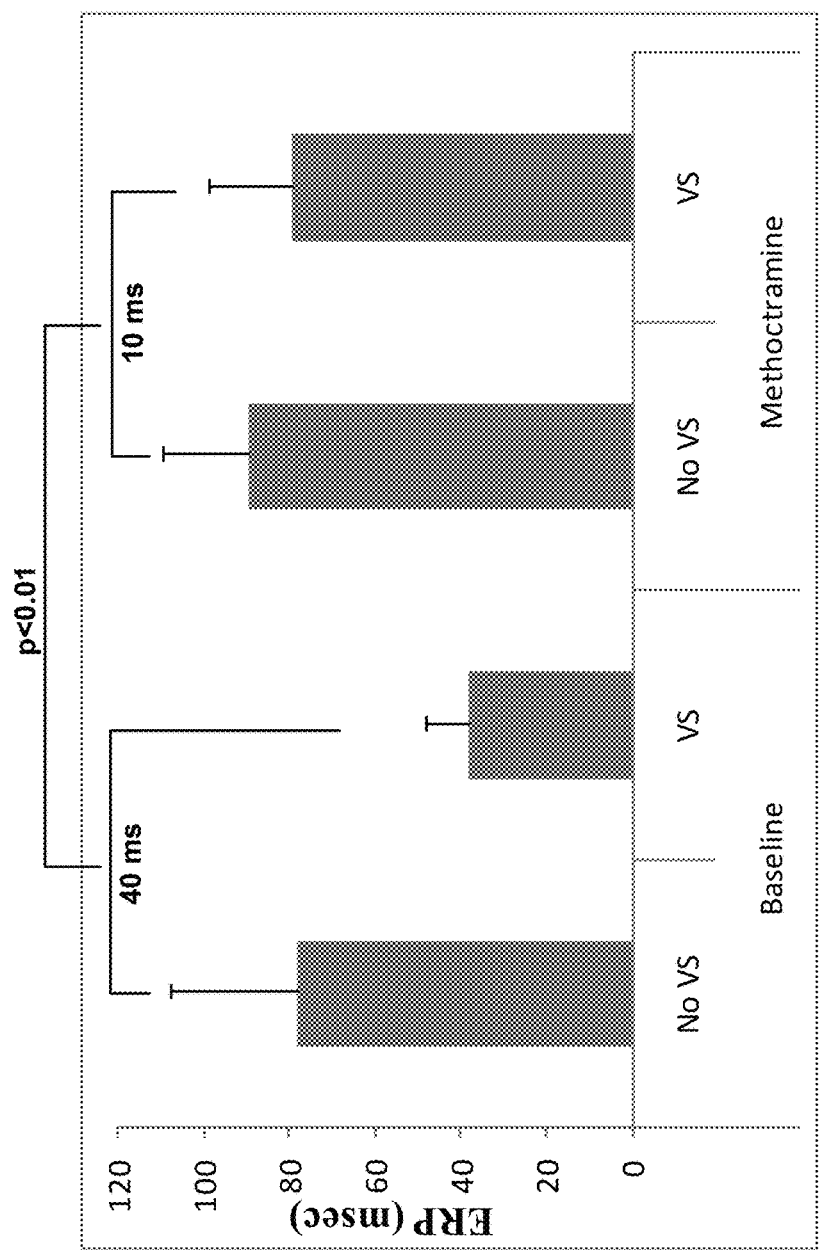
FIG. 3 shows the effects of methoctramine, a $M_2$-selective muscarinic receptor blocker, on the effective refractory period (ERP) shortening caused by vagal stimulation in a canine model.
Figure 4:
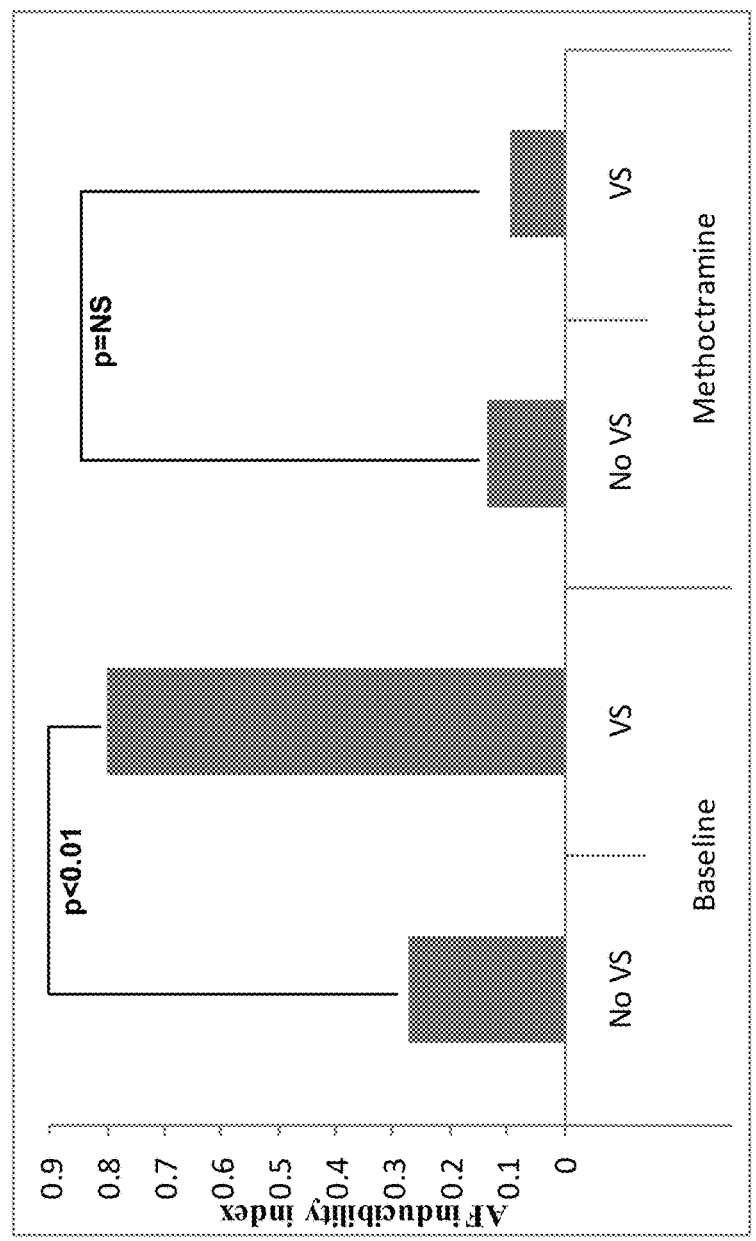
FIG. 4 shows the effects of methoctramine, a $M_2$-selective muscarinic receptor blocker, on atrial fibrillation caused by vagal induction in a canine model.

Vagal induced ERP shortening was significantly decreased by methoctramine (40 ms vs 10 ms, p<0.01; y-axis shows ERP in milliseconds) (SEE FIG. 3). Vagal induced AF was also markedly decreased by methoctramine (SEE FIG. 4).

All publications and patents mentioned in the present application and/or listed below are herein incorporated by reference. Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims.

What is claimed is:

1. A method of treating, reversing, and/or preventing cardiac arrhythmia in a human subject comprising co-administering a therapeutically effective amount of a beta-adrenergic receptor blocking agent and a therapeutically effective amount of a muscarinic receptor blocking agent directly to the surface of the heart of said human subject.

2. The method of claim 1, wherein said beta-adrenergic receptor blocking agent is selected from the group consisting of aprenolol, carteolol, levobunolol, mepindolol, metipranolol, nadolol, oxprenolol, timolol, sotalol, esmolol, cateolol, propranolol, betaxolol, penbutolol, metoprolol, acebutolol, atenolol, metoprolol, pindolol, bisoprolol, nebivolol, amosulalol, landiolol, and tilisolol, including any salts, hydrates, solvates, prodrugs, and any crystal forms in which they may occur.

3. The method of claim 1, wherein said muscarinic receptor blocker is selected from the group comprising atropine, scopolamine, ipratropium, tropicamide, pirenzepine, diphenhydramine, dimenhydrinate, dicyclomine, oxybutynin, tiotropium, cyclopentolate, atropine methonitrate, trihexyphenidyl, tolterodine, solifenacin, darifenacin, benzatropine, and mebeverine, including any salts, hydrates, solvates, prodrugs, and any crystal forms in which they may occur.

4. The method of claim 1, wherein said muscarinic receptor blocker is a M2-selective muscarinic receptor subtype.

5. The method of claim 1, wherein said cardiac arrhythmia comprises atrial fibrillation.

6. The method of claim 1, wherein said beta-adrenergic receptor blocking agent is not esmolol.

7. A method of treating, reversing, and/or preventing cardiac arrhythmia in a human subject comprising administering a therapeutically effective amount of an M2-selective muscarinic receptor blocking agent directly to the surface of the heart of said human subject.

8. The method of claim 7, wherein the cardiac arrhythmia is atrial fibrillation.

9. The method of claim 7, wherein said M2-selective muscarinic receptor blocking agent selectively blocks the M2 receptor subtype by at least five-fold versus the M3 receptor subtype.

10. The method of claim 9, wherein said M2-selective muscarinic receptor blocking agent selectively blocks the M2 receptor subtype by at least five-fold versus the M1 receptor subtype.

11. The method of claim 7, wherein said M2-selective muscarinic receptor blocking agent is selected from Sch 211803, TD-6301, and methoctramine.

12. The method of claim 1, wherein said beta-adrenergic receptor blocking agent is propranolol.

13. The method of claim 12, wherein said muscarinic receptor blocking agent is atropine.

14. A method of treating, reversing, and/or preventing cardiac arrhythmia in a human subject comprising co-administering directly to the surface of the heart of said human subject a therapeutically effective amount of a beta-adrenergic receptor blocking agent and a therapeutically effective amount of a muscarinic receptor blocking agent, wherein said beta-adrenergic receptor blocking agent is selected from the group consisting of esmolol aprenolol, carteolol, levobunolol, mepindolol, metipranolol, nadolol, oxprenolol, timolol, sotalol, cateolol, propranolol, betaxolol, penbutolol, metoprolol, acebutolol, atenolol, metoprolol, pindolol, bisoprolol, nebivolol, amosulalol, landiolol, and tilisolol, including any salts, hydrates, solvates, prodrugs, and any crystal forms in which they may occur.

* * * * *